(12) United States Patent
Wang et al.

(10) Patent No.: US 8,119,704 B2
(45) Date of Patent: Feb. 21, 2012

(54) IMPLANTABLE MEDICAL DEVICE COMPRISING COPOLYMER OF L-LACTIDE WITH IMPROVED FRACTURE TOUGHNESS

(75) Inventors: Yunbing Wang, Sunnyvale, CA (US); James Oberhauser, Saratoga, CA (US); Manish Gada, Santa Clara, CA (US); Thierry Glauser, Redwood City, CA (US); Vincent Gueriguian, San Francisco, CA (US); Bethany Steichen, San Francisco, CA (US); Lothar Kleiner, Los Altos, CA (US); Xiao Ma, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 117 days.

(21) Appl. No.: 12/506,881

(22) Filed: Jul. 21, 2009

(65) Prior Publication Data

US 2011/0022163 A1    Jan. 27, 2011

(51) Int. Cl.
*A61F 2/06* (2006.01)
*A61F 2/02* (2006.01)
*C08G 63/08* (2006.01)

(52) U.S. Cl. ....... 523/113; 528/354; 623/1.38; 623/1.49
(58) Field of Classification Search .................. 523/113; 528/354; 264/235; 623/1.38, 1.49
See application file for complete search history.

(56) References Cited

U.S. PATENT DOCUMENTS

| | | | | |
|---|---|---|---|---|
| 3,636,956 A * | 1/1972 | Schneider | ...... | 606/224 |
| 6,607,548 B2 * | 8/2003 | Pohjonen et al. | ...... | 606/230 |
| 6,932,930 B2 * | 8/2005 | DeSimone et al. | ...... | 264/235 |
| 7,572,287 B2 * | 8/2009 | Stinson | ...... | 623/1.15 |
| 7,842,737 B2 * | 11/2010 | Wang et al. | ...... | 523/113 |
| 7,846,361 B2 * | 12/2010 | Thatcher et al. | ...... | 264/148 |
| 2003/0114637 A1 * | 6/2003 | Gogolewski | ...... | 528/354 |
| 2003/0219562 A1 * | 11/2003 | Rypacek et al. | ...... | 428/36.91 |
| 2007/0014848 A1 * | 1/2007 | Buchholz et al. | ...... | 424/456 |
| 2007/0179253 A1 * | 8/2007 | Matsuoka et al. | ...... | 525/438 |
| 2008/0051868 A1 * | 2/2008 | Cottone et al. | ...... | 623/1.11 |
| 2008/0081063 A1 * | 4/2008 | Wang et al. | ...... | 424/426 |
| 2008/0118546 A1 * | 5/2008 | Thatcher et al. | ...... | 424/426 |
| 2008/0177374 A1 * | 7/2008 | Zheng et al. | ...... | 623/1.15 |
| 2008/0262150 A1 * | 10/2008 | Takenaka et al. | ...... | 524/599 |
| 2009/0110713 A1 * | 4/2009 | Lim et al. | ...... | 424/423 |
| 2009/0263457 A1 * | 10/2009 | Trollsas et al. | ...... | 424/426 |
| 2010/0158969 A1 * | 6/2010 | Tice | ...... | 424/422 |
| 2010/0291175 A1 * | 11/2010 | Trollsas et al. | ...... | 424/423 |

FOREIGN PATENT DOCUMENTS

WO    WO 2008/089434    7/2008

OTHER PUBLICATIONS

Anderson et al., "Melt preparation and nucleation efficiency of polylactide stereocomplex crystallites", Polymer vol. 47, issue 6, pp. 2030-2035 (2006) Abstract 1 pg.
"Synthetic polymers, polypeptides & other biopolymers/ poly(glycolides) and Poly(lactides)", Poly(glycolides) and Poly(lactides) downloaded from: www.carbomer.com/cart/catalog/ Poly_glycolides_and_poly_lactides, Jun. 13, 2009, 1 pg.
Schmidt et al., "Polylactide stereocomplex crystallites as nucleating agents for isotactic polylactide", J. of Pol. Science Part B. vol. 39, No. 3, pp. 300-313 (2001) Abstract 1 pg.
International Search Report for PCT/US2010/041996, mailed Mar. 21, 2011, 8 pgs.
Välimaa et al., "Viscoelastic memory and self-expansion of self-reinforced bioabsorbable stents", Biomaterials 23, pp. 3575-3582 (2002).

* cited by examiner

*Primary Examiner* — Tae H Yoon
(74) *Attorney, Agent, or Firm* — Squire Sanders (US) LLP

(57) ABSTRACT

The present invention relates to implantable medical devices comprising a L-lactide-constitutional unit-containing copolymer having a wt % percent crystallinity of 40% or less.

6 Claims, No Drawings

IMPLANTABLE MEDICAL DEVICE COMPRISING COPOLYMER OF L-LACTIDE WITH IMPROVED FRACTURE TOUGHNESS

FIELD

This invention relates to the fields of polymer chemistry, material science and implantable medical devices.

BACKGROUND

In the field of implantable medical devices polymers based on L-lactic acid are quite favored due to the excellent biocompatibility of lactic acid. That is, lactic acid polymers biodegrade to smaller fragments and eventually to small molecules that are generally well-tolerated by the mammalian system.

When synthesizing poly(lactic acid) it is possible to use lactic acid itself as the monomer. The molecular weight of the polymer, however, is limited and if higher molecular weight product is desired, lactide, the dimer of lactic acid is the preferred monomer. For the purposes of this disclosure, poly(lactide) will be used to signify that the resultant polymers may have a broad range of molecular weights.

Constructs made of poly(lactide) exhibit good mechanical characteristics such as strength and tensile modulus. The fracture toughness of poly(lactide) is, however, lower than is often desired in a particular construct such as stents. The high strength and tensile modulus and concomitant low fracture toughness stems from the high degree of crystallinity of poly(lactide), which can be 55% or greater depending on polymer synthesis, construct-forming polymer formulation and construct fabrication parameters. In addition to the relatively high percent crystallinity, the crystalline structure of poly(lactic acid) in general comprises relatively large spherulites that add to the strength and tensile modulus of the polymer but detract from the fracture toughness.

What is needed is a lactide-based composition that can be fabricated into an implantable medical device that exhibits good strength, a good tensile modulus and good fracture toughness. The present invention provides such a composition and implantable medical devices fabricated of that composition.

SUMMARY

Thus, an aspect of this invention is an implantable medical device, comprising a copolymer comprising L-lactide and a second monomer wherein the resulting copolymer has a crystallinity of 40% or less.

In an aspect of this invention, the crystallinity of the copolymer is from about 5% to about 35%.

In an aspect of this invention, the crystallinity of the copolymer is from about 15% to about 25%.

In an aspect of this invention, the second monomer comprises from about 1 mol % to about 10 mol % D-lactide; or from about 1 mol % to about 10 mol % glycolide; or from about 1 mol % to about 10 mol % ε-caprolactone; or from about 1 mol % to about 10 mol % trimethylene carbonate; or from about 1 mol % to about 10 mol % dioxanone; or any combination of the above wherein the total mol % of the second monomer is about 1 mol % to about 10 mol %.

In an aspect of this invention, the copolymer comprises about 4 mol % to about 5 mol % of the second monomer.

In an aspect of this invention, the copolymer comprises glycolide-derived and ε-caprolactone-derived constitutional units.

In an aspect of this invention, the mol % of glycolide-derived constitutional unit in the copolymer is about 2 mol % and the mol % of the ε-caprolactone-derived constitutional unit in the copolymer is about 3 mol %.

In an aspect of this invention, the copolymer comprises D-lactide.

In an aspect of this invention, the implantable medical device further comprises blending with the above D-lactide-containing copolymer about 2 wt % to about 10 wt % of poly(D-lactide) based on the total weight of copolymer plus poly(D-lactide).

In an aspect of this invention, the wt % of poly(D-lactide) blended with the copolymer is substantially the same as the wt % of D-lactide monomer in the copolymer.

In an aspect of this invention, the implantable medical device comprises poly(L-lactide-co-glycolide) blended with about 2 wt % to about 10 wt % of poly(D-lactide-co-glycolide) based on the total weight of copolymer plus poly(D-lactide-co-glycolide) wherein the poly(D-lactide-co-glycolide) comprises about 1 mol % to about 10 mol % glycolide monomer.

In an aspect of this invention, the implantable medical device comprises poly(L-lactide-co-ε-caprolactone) blended with about 2 wt % to about 10 wt % of poly(D-lactide-co-ε-caprolactone) based on the total weight of copolymer plus poly(D-lactide-co-ε-caprolactone) wherein the poly(d-lactide-co-ε-caprolactone) comprises about 1 mol % to about 10 mol % of ε-caprolactone monomer.

In an aspect of this invention, the implantable medical device comprises poly(L-lactide-co-dioxanone) blended with about 2 wt % to about 10 wt % of poly(D-lactide-co-dioxanone) based on the total weight of copolymer plus poly(D-lactide-co-dioxanone) wherein the poly(D-lactide-co-dioxanone) comprises about 1 mol % to about 10 mol % of dioxanone.

In an aspect of this invention the implantable medical device comprises a stent.

An aspect of this invention is a method of fabricating a stent, comprising providing a copolymer of claim 1; optionally, adding a nucleating agent to the copolymer; extruding the copolymer to form a tube; annealing the extruded tube; expanding the annealed tube radially, axially or biaxially or any combination thereof; and forming the implantable medical device from the expanded tube.

In an aspect of this invention, the above method comprises adding the nucleating agent to the copolymer.

In an aspect of this invention, the nucleating agent is selected from the group consisting of talc, magnesium silicate hydrate, ethylene bis (1,2-hydroxystearylamide), hydroxyapatite, decamethylene-dicarboxylichydrazide, dibenzoylhydrazide, dioctyl phthalate, ethyl lactate, citric acid esters, lactic acid esters, lactide esters, triphenyl phosphate, glycerine, acetin, butyrin and a fatty acid.

In an aspect of this invention no nucleation agent is added to the polymer melt but the extruded tube is annealed.

DETAILED DESCRIPTION

It is understood that use of the singular throughout this application including the claims includes the plural and vice versa unless expressly stated otherwise. That is, "a" and "the" are to be construed as referring to one or more of whatever the word modifies. Non-limiting examples are: "a therapeutic agent," which is understood to include one such agent, two such agents or, under the right circumstances, as determined by those skilled in the treatment of diseased tissues, even more such agents unless it is expressly stated or is unambiguously obvious from the context that such is not intended. Likewise, "a biodegradable polymer" refers to a single polymer or a mixture of two or more polymers unless, again, it is expressly stated or absolutely obvious from the context that such is not intended.

As used herein, unless specified otherwise, any words of approximation such as without limitation, "about," "essentially," "substantially" and the like mean that the element so modified need not be exactly what is described but can vary from exact compliance with the written description by as much as ±15% without exceeding the scope of this invention.

As used herein, the use of "preferred," "preferably," or "more preferred," and the like refer to modify an aspect of the invention refers to preferences as they existed at the time of filing of the patent application.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts. At present, preferred implantable medical devices for use with the coatings of this invention are stents.

A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable.

As used herein, "optional" means that the element modified by the term may, but is not required to, be present.

A polymer of this invention may be a homopolymer, a copolymer, a star polymer, a dendritic polymer (dendrite) or a graft polymer, although presently preferred are homopolymers and copolymers.

A homopolymer simply refers to a polymer comprising a single monomer, a monomer simply being a molecule that is iteratively reacted with itself to form chains of constitutional units, i.e., a polymer. A copolymer refers to a polymer prepared from two or more monomers that may be reacted so as to form random copolymers, regular alternating copolymers, random alternating copolymers, regular block copolymers or random block copolymers. A random copolymer has the general structure, assuming three monomers/constitutional units, x-x-y-x-z-y-y-x-z-y-z- . . . , while a regular alternating copolymer has the general structure: . . . x-y-z-x-y-z-x-y-z- . . . and a random alternating copolymer has the general structure: . . . x-y-x-z-x-y-z-y-z-x-y- . . . , it being understood that the juxtaposition of constitutional units shown here is for purpose of illustration only and a copolymer of this invention may vary from that shown. A regular block copolymer has the general structure: . . . x-x-x-y-y-y-z-z-z-x-x-x . . . , while a random block copolymer has the general structure: . . . x-x-x-z-z-x-x-y-y-y-z-z-z-x-x-z-z-z- . . . . Similarly to random and regular and alternating copolymers, the juxtaposition of blocks, the number of constitutional units in each block and the number of blocks in a block copolymer of this invention are not in any manner limited by the preceding illustrative generic structures. In fact, presently preferred polymers of this invention are either homopolymers or random two-monomer copolymers but the general principles above still pertain.

As used herein a "constitutional unit" refers to the repeating structure in a polymer backbone, the constitutional unit resulting from the reaction of monomers. For example, without limitation, a poly(L-lactide), is prepared by the polymerization of the monomer L-lactide:

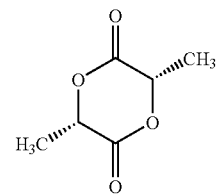

while the constitutional unit derived therefrom is

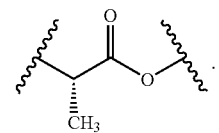

When a polymer chain comprises sufficient structural regularity, it may come together with other polymer chains in an aligned configuration and ultimately form crystalline structures. Without being held to any particular theory, polymer crystallization is believed to follow the classical growth pattern of crystalline small molecules. That is, crystallization begins with nucleation, the formation of small crystalline particles around a bit of debris in the sea of liquid polymer. These nuclei grow in a hierarchy of ordered structures, namely into lamellae and, eventually, into spherulites. It is noted that spherulite formation is the classical structure obtained during quiescent crystallization. If strain is imparted during the crystallization process, crystallization will be more complex, resembling an jumble of assorted lamellae. If highly strained, a shish-kabab structure may develops that includes a large number of crystal imperfections. For the purposes of this disclosure, the term "spherulite" or "spherulites" will be understood to refer to the classical crystal form as well as to whatever crystalline formations are created as the result of subjecting a subject polymer to strain by radial and/or biaxial orientation. The crystalline regions of polymers exhibit considerable long-range order when subjected to x-ray diffraction examination. The crystalline regions of polymers are quite robust and will maintain a physically crosslinked configuration until the melting point, $T_m$, which is a relatively determinate number, of the crystalline regions is reached at which time the crystal structures "melt" similarly to small molecules crystals and become amorphous. Few polymers are 100% crystalline; rather they tend to have discrete regions of crystalline structures and other regions that are amorphous. Thus, the crystalline polymer segments of this invention are referred to as crystalline or semi-crystalline, the latter term referring to a segment that is predominantly but not necessarily completely crystalline.

Crystallinity imparts beneficial properties on a polymer such as strength and tensile modulus. Polymers with a high degree of crystallinity, that is, crystallinity greater than about 50%, tend, however, to exhibit low fracture toughness and are usually characterized as brittle. Pure poly(L-lactide) fits into this category of high crystallinity/low fracture toughness polymers. In fact, in stents formed by extrusion of pure poly(L-lactide) into a tube configuration followed by expansion to increase it biaxial orientation, the polymeric device has been found to be about 55% crystalline.

Since L-lactide is a preferred implantable medical device polymer raw material, reducing the crystallinity of L-lactide-containing polymers in constructs is highly desirable. Such may be accomplished by adding small amounts of a second monomer to the L-lactide polymerization reaction. Copolymers that retain the desirable mechanical properties of poly(L-lactide) but which exhibit much improved fracture toughness can be prepared in this manner. It is presently preferred that an L-lactide-containing semi-crystalline copolymer useful in the fabrication of implantable medical devices, in particular, stents, have a crystallinity of about 10% to about 40%, preferably about 20% to about 40% and more preferably still, about 30% to about 40%.

Monomers that can be added to L-lactide to provide a polymer with reduced crystallinity and concomitantly increased elasticity include, without limitation: D-lactide, prepared from the other enantiomer of lactic acid;

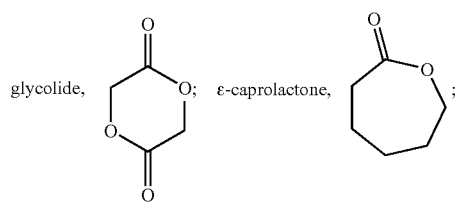

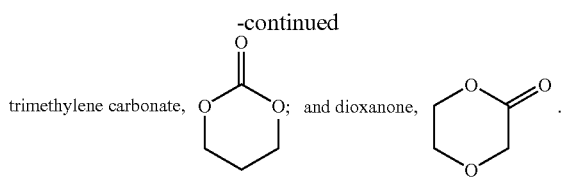

The second monomers can be added to the polymerization in relatively small amounts, about 1 mol % to about 10 mol %, preferably about 4 mol % to about 8 mol %, more preferably about 5%.

In addition to providing an L-lactide-containing polymer with reduced crystallinity over poly(L-lactide), adding glycolide monomer in the amounts disclosed above has the additional beneficial effect of providing a polymer with an increased biodegradation rate relative to that of pure poly(L-lactide).

The effect of glycolide on the biodegradation rate of the resultant polymer can be modified by reducing its percentage in the polymer and replacing it with one of the other monomers disclosed above, which monomers have the desired effect on crystallinity but do not substantially affect biodegradation rate. Thus, as a non-limiting example, about 2 mol % glycolide and 3 mol % ε-caprolactone and about 95 mol % lactide can be random polymerized to provide a polymer with both enhanced fracture toughness and increased biodegradation rate.

As used herein, "biodegradation rate" refers to the rate of decomposition of a polymer under physiological conditions of temperature, pH, enzymatic activity, etc.

In addition to providing a polymer containing predominantly the biologically-preferred L-lactide-derived constitutional unit but with reduced overall crystallinity over pure poly(L-lactide), it also may be beneficial to reduce the size of the crystalline structures, which, without being bound to any particular theory, may amount to a reduction in the thickness of stress-induced lamellar crystalline structures, formed when the L-lactide segments of the copolymer crystallize. This can be accomplished by several means. During the mechanical processing of a polymer herein, the polymer melt is extruded and then expanded to increase its biaxial orientation. If, after extrusion and prior to expansion, the polymer tube is annealed at a temperature just about the polymer's $T_g$, during the process the number of crystallization nuclei increases, giving rise to more but smaller spherulites. The actual percentage crystallinity may not by this process be substantially altered but the smaller crystalline structures endow the polymer with less brittleness.

One relatively common means of increasing the number of crystallization nuclei is to physically add particulate matter to the polymerization or to the polymer melt before extrusion. While virtually any type of particle that is compatible with L-lactide and poly(L-lactide) and is biocompatible can be used, a few non-limiting examples include talc, which has a very small particle size—1 μm or less—is readily obtainable and can be used to effect nucleation of spherulite formation in a variety of semi-crystalline polymers; magnesium silicate hydrate, ethylene bis(1,2-hydroxystearylamide), hydroxyapatite, decamethylene-dicarboxylichydrazide, dibenzoylhydrazide, dioctyl phthalate, ethyl lactate, citric acid esters, lactic acid esters, lactide esters, triphenyl phosphate, glycerine, acetin, and butyrin.

Another means of reducing overall spherulite size is to employ the phenomenon of stereocomplex formation. A "stereocomplex" refers to a specific interaction between two complementary polymeric structures that interlock into a new composite that possesses different physical characteristics from the individual polymers. "Complementary" structures refers to two polymers that are homopolymers of the individual enantiomers of an optically active molecule such that each polymer is optically active. "Complementary" can also refer to two polymers that bear similar but not identical chemical structures in which case the polymers relate to one another as diasteromers rather than enantiomers. Even further, "complementary" can even refer to unrelated but optically active polymers of opposite polarity that are capable of forming stereocomplexes in which case the stereocomplex is called a "hetero-stereocomplex." For example, without limitation, a heterostereocomplex can be formed between poly(D-lactide) and L-configured polypeptides. All types of stereocomplexes, so long as both participating polymer are biocompatible, are within the scope of this invention.

As used herein, "biocompatible" refers to a polymer that both in its intact, i.e. as synthesized, state and in its decomposed state, i.e., and in its biodegraded state, is not, or at least is minimally, toxic to living tissue; does not, or at least minimally and reparably, injure(s) living tissue; and/or does not, or at least minimally and/or controllably, cause(s) an immunological reaction in living tissue.

While any stereoselective, i.e., optically active, biocompatible polymer that is capable of forming stereocomplexes may be used to alter the crystallinity of an L-lactide-containing polymer, a presently preferred polymer is poly(D-lactide). Thus, blending about 2 wt % to about 5 wt % of poly(D-lactide) with poly(L-lactide-co-D-lactide) containing about 5 mol % D-lactide results in stereocomplex formation during the extrusion process. The sites of stereocomplexation can act a nucleation sites for crystallite formation and, similar to the results obtained when nucleation sites are formed by annealing or particle addition, the resulting spherulites are smaller and therefore cause less brittleness than do larger spherulites.

Parameters that can affect stereocomplexation and therefore can be used in the fabrication of implantable medical devices of this invention include, without limitation, the presence or absence of additives (plasticizers, fillers, stabilizers, etc.) in the composition, the mixing process, applied temperatures, the molding process, any annealing process that might be employed, the solvents used, cooling and heating cycles, pressure and mechanical forces applied and irradiation such as might be applied during sterilization of a implantable medical device. The manipulation and interrelationship among these various parameters are well-known to those of ordinary skill in the art and need not be further explicated herein; the skilled artisan will be able to apply the parameters to achieve the desired results based on the disclosures herein.

Stereocomplex formation can also be achieved using a copolymer of D-lactide rather than pure poly(D-lactide) to interact with a copolymer of L-lactide. Thus, for example without limitation, adding about 2 mol % to about 5 mol % of poly(D-lactide-co-glycolide) containing about 2 mol % to about 5 mol % glycolide to poly(L-lactide-co-glycolide) containing about 2 mol % to about 5 mol % glycolide will likewise result in stereocomplex formation during extrusion resulting, as discussed above, smaller spherulites and a correspondingly less brittle polymer construct.

An aspect of this invention is a method of fabricating a stent from the L-lactide-based polymers disclosed herein. The method involves optionally adding a nucleating agent to a polymer melt, extruding the melt to form a tubular structure, optionally annealing the tubular structure, expanding the extruded or annealed tube and then forming the stent from the tube using techniques such as, without limitation, femtolaser cutting. If a nucleating agent is added to the polymer melt, annealing is optional and similarly if the extruded polymeric tube is to be annealed, addition of a nucleating agent is optional. If desired both the nucleating agent and annealing may be included in the stent forming process.

EXAMPLES

Example 1

Synthesis of poly(l-lactide-co-(5 mol %)D-latide)

In an 2 liter reactor, 500 g of L-lactide, 25 g D-lactide, 0.54 ml docecanol initiator and 2.24 mL stannous octanoate are mixed together with mechanical stirring. The reactor is purged with nitrogen and then the mixture is heated with stirring at 160° C. for one hour. Stirring is then ceased and the reaction is allowed to continue at 160° C. for an additional 5 hours. The reactor is then cooled, the solid polymer is removed, chopped into small pieces and stirred with methanol for 4 hours to remove unreacted monomers. The product is then dried in a vacuum oven at 80° C. to constant weight.

Example 2

Synthesis of poly(L-lactide-co-(3 mol %)ϵ-caprolactone-co-(2-mol %)glycolide)

In an 2 liter reactor, 500 g of L-lactide, 10 g glycolide, 15 g ϵ-caprolactone, 0.54 ml docecanol initiator and 2.24 mL stannous octanoate are mixed together with mechanical stirring. The reactor is purged with nitrogen and then the mixture is heated with stirring at 160° C. for two hours. Stirring is then ceased and the reaction is allowed to continue at 160° C. for an additional 10 hours. The reactor is then cooled, the solid polymer is removed, chopped into small pieces and stirred with methanol for 4 hours to remove unreacted monomers. The product is then dried in a vacuum oven at 80° C. to constant weight.

Example 3

Stent Fabrication

Using either of the above polymers, a quantity of the polymer is extruded in a single-screw extruder at about 200° C. and the extruded tubing is quickly quenched in cold water to give a tube having an ID of 0.02" and an OD of 0.06". At this point, the extruded tubing can be annealed at about 70° C. for 0.5 to about 5 hours to increase nucleation density and resulting smaller spherulite size. The extruded or extruded/annealed tubing is placed in a glass mold and expanded at about 180° F. to increase biaxial orientation. The final ID of the tube is 0.12" and the final OD is 0.13".

A stent may be cut from the expanded tubing using a femto-second laser, crimped on a balloon catheter to an overall size of 0.05" and sterilized by electron beam at a dose of 25 kGy.

What is claimed is:
1. An implantable medical device, comprising:
a copolymer comprising:
L-lactide and from about 4 mol % to about 5 mol % glycolide, wherein the copolymer has a crystallinity from about 20 wt % to about 30 wt % prior to fabrication into the device; the copolymer being blended with about 2 wt % to about 10 wt % poly(D-lactide-co-glycolide) based on the total weight of copolymer plus poly(D-lactide- co-glycolide) wherein the poly(D-lactide-co-glycolide) comprises about 2 mol % to about 10 mol % glycolide monomer.

2. The implantable medical device of claim 1, comprising a stent.

3. An implantable medical device, comprising:
a copolymer comprising:
L-lactide and from about 1 mol % to about 10 mol % ε-caprolactone, wherein the copolymer has a crystallinity from about 20 wt % to about 30 wt % prior to fabrication into the device; the copolymer being blended with about 2 wt % to about 10 wt % poly(D-lactide-co-ε-caprolactone) based on the total weight of copolymer plus poly(D-lactide-co-ε-caprolactone) wherein the poly(D-lactide-co-ε-caprolactone) comprises about 2 mol % to about 10 mol % ε-caprolactone monomer.

4. The implantable medical device of claim 3, comprising a stent.

5. An implantable medical device, comprising:
a copolymer comprising:
L-lactide and from about 1 mol % to about 10 mol % dioxanone, wherein the copolymer has a crystallinity from about 20 wt % to about 30 wt % prior to fabrication into the device; the copolymer being blended with about 2 wt % to about 10 wt % poly(D-lactide-co-dioxanone) based on the total weight of copolymer plus poly(D-lactide-co-dioxanone) wherein the poly(D-lactide-co-dioxanone) comprises about 2 mol % to about 10 mol % dioxanone monomer.

6. The implantable medical device of claim 5, comprising a stent.

* * * * *